United States Patent
Agblevor et al.

(10) Patent No.: US 7,217,545 B2
(45) Date of Patent: May 15, 2007

(54) METHOD FOR PRODUCTION OF LACTIC ACID

(75) Inventors: Foster A. Agblevor, Blacksburg, VA (US); Timothy G. Evans, Blacksburg, VA (US)

(73) Assignee: Wessex Incorporated, Blacksburg, VA (US)

( * ) Notice: Subject to any disclaimer, the term of this patent is extended or adjusted under 35 U.S.C. 154(b) by 699 days.

(21) Appl. No.: 10/438,244

(22) Filed: May 14, 2003

(65) Prior Publication Data

US 2004/0229327 A1 Nov. 18, 2004

(51) Int. Cl.
C12P 7/56 (2006.01)
C12P 7/40 (2006.01)
C12P 1/00 (2006.01)

(52) U.S. Cl. .................. 435/139; 435/136; 435/41
(58) Field of Classification Search ............... 435/139, 435/136, 41
See application file for complete search history.

(56) References Cited

U.S. PATENT DOCUMENTS

| | | | |
|---|---|---|---|
| 5,464,760 A | 11/1995 | Tsai et al. | |
| 5,932,455 A | 8/1999 | Viljava et al. | |
| 6,280,985 B1 | 8/2001 | Caboche et al. | |
| 6,319,382 B1 | 11/2001 | Norddahl | |

FOREIGN PATENT DOCUMENTS

WO  WO 00/53791  * 9/2000

OTHER PUBLICATIONS

Woiciechowski et al (Process Biochemistry 34:949-955 (1999)).*
Abe, S., Takagi, M., Communications to the Editor: Simulatanaeous Saccrhaification and feremntation of Cellulose to Lactic Acid, Biotech & Engineering, Jan. 1991, 32:93-95.
Chang, M.M.; Chou, Y.C.T.; Tsao, G.T., Structure, Pretreatment and Hydrolsys of Cellulose, Adv. Biochem. Eng., 1981, 20:15-42.
Chum, H.L;Douglas;L.J.;Reinberg, D.D.;Schroeder, H.A., Evaluation of pretreatments of biomass for enzymatic hydrolysis of cellulose, SERI/TP-231-2183, 1985, SERI. Golden, CO.
Dale, B.E., Annual Reports on Fermentation Processes, 1985, vol. 1, 8, 299-232.
Danner, H.; Madzingaidzo, L.;Harti, A.; Thermophilic fermentative production of lactic acid from C5-sugars, Biomass for Energy and Industry, C.R.M.E.N. 1998, 446-449.
Danner,H.;Neureiter,L.;Madzingaidzo,M.;Gartner,M.Braun,R., *Bacillus stearotherm-ophilus* for Thermophilic Production of L-Lactic Acid,Appl.Biochem.Biotechn, 1998,70/72:895-903.
Dekker, R.F.H. Steam explosion: An effective pretreatment method for use in the bioconversion of lignocellulosic materials, 1991, 277-305.
Fan, L.T.; Lee, Y.H.; Gharpuray, M.M., The Nature of Lignocellulosics and Their Pretreatments for Enzymatic Hydrolysis; Adv. Biochem. Eng. 23; 157-187.
Gnanasanbandam, M.M.; Proctor, A.; Structure and Performance of Soy Hull Carbon Adsorbents as Affected by Pyrolysis Temperature, Jaocs, 1998. 75: 5:615-621.
Gruber, P.; O'Brien, M.; Polylactides "NatureWorks ™PLA" Polyesters III: Applications and Commercial Products, Biopolymers, 4:8 235-239, Minnetonka, MN.
Hicks, K.B.; Moreau, R.A.; Donrer, L.W.;Corn fiber; an old by-product with a cornucopia of future uses, in Proc. Corn Utilization Conf. Jun. 4-6, 1996. St Louis, MO.
Lin.K.W.;Ladisch,M.R.,Schaefer,D.M.;Noller,C.H.;Lechtenberg,V. ;Tsao,G.T.;1981,Review on Effect of Pretreatment on Digestibility of Cellulosic Materials,AlChE Symp.207,77:102-6.
Marshall,W.E.;Wartelle,L.H.;Boler,D.E.;Johns,C.A., TOLES;Enhanced metal adsorption by soybean hulls modified with citric acid, Bioresource Technology,1999:69:263-8.
McMillan, J. D.; Pretreatment of lignoccellulosic biomass. ACS-smp.ser. KWahsing to DC; American Chemical Society 1998(566), 292-153.
Tsal, S-P., "Food-Processing Waste Converted to Valuable Chemical Products," Argonne National Laboratory Web Site, http://www.es.anl.gov/htmls/food.process.html.
Yan,J.;Bajpai,R.;Iannotti,E.;Popovic,M.;Mueller,R.,LacticAcidFermentationFromEnzyme-Thinned StarchWith Immobilized *Lactobacillus amylovorus*,Chem.Biochem.Eng.Q.2001, 15(2)59-63.
Unk; Focus report: Emerging markets 98: Carbohydrate feedstocks: Renewing interest in agricultural-based feedstocks, Chemical Market Reporter,254,19,981109,FR14.
Unk, Agriculture-Industry of the Future, Office of Industrial Technologies, Office of Energy Efficiency and Renewable Energy, U.S. Dept. of Energy, 2001.
Unk, Biodegradable and Biorenewable Materials Based on Lactic Acid, Lactide, 1-3.

* cited by examiner

*Primary Examiner*—B. Dell Chism
(74) *Attorney, Agent, or Firm*—Mary-Jacq Holroyd; Johnston Holroyd

(57) ABSTRACT

A method for production of lactic acid involving extracting protein from a natural renewable feedstock, preferably extracted from lignocellulose sources such as soybean hull, separating the feedstock into liquid and solid substrate feedstock, steam exploding the solid substrate feedstock by placing the solid feedstock in a pressure chamber, pressurizing the steam chamber with saturated steam, maintaining the pressure until the solid feedstock reaches temperatures in excess of the boiling point of water at atmospheric pressure, and explosively decompressing the pressure to a pressure no greater than atmospheric pressure. Hydrolyzing the steam-exploded feedstock by either acid hydrolysis or enzyme hydrolysis, and fermenting the resulting hydrolyzed feedstock to produce lactic acid. The hydrolyzing and fermenting steps may be carried out simultaneously, followed by recovering the lactate from the resultant material.

20 Claims, 1 Drawing Sheet

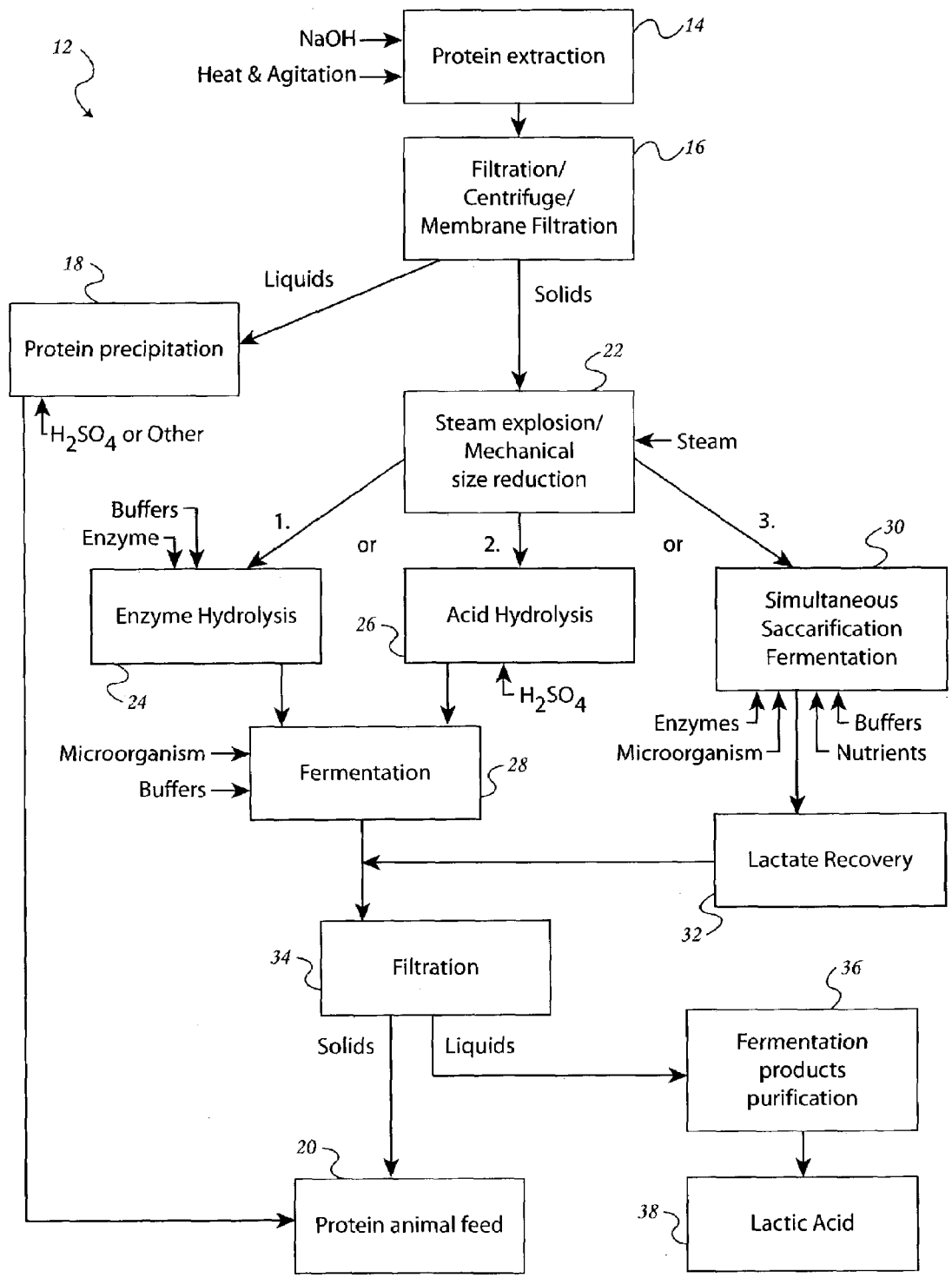

METHOD FOR PRODUCTION OF LACTIC ACID

FIELD OF THE INVENTION

The present invention relates to a method of producing lactic acid, and in particular, to a method of producing lactic acid from renewable resources such as soybean hulls.

BACKGROUND OF THE INVENTION

Lactic acid is a methyl-substituted glycolic acid that has been generated by fermentation of renewable agricultural feedstock resources such as corn, whey, potatoes, rice, cane sugar, beet sugar, molasses of beet-sugar, and the like. Lactic acid is the simplest hydroxyl acid having an asymmetric carbon atom and therefore exists in a racemic form and in two optically active forms.

Two molecules of lactic acid combine to form the monomer (dilactide) for a polymer called polylactic acid, which is a biodegradable and biorenewable material. When dilactide is prepared from racemic lactic acid, the three isomers that result are D-lactide, L-lactide and meso-lactide. The meso isomer can be removed but the D and L-lactide are enatiomers that from the racemic form, rac-lactide, which forms an undesirable amorphous polymer. Most commercial processes use the L-lactide produced from L-lactic acid.

There are numerous uses for lactic acid. It is a common food additive as an acidulant and preservative, and is used in the chemical industry for deliming, metal etching, cosmetic and textile applications, oxychemicals, green solvents, specialty chemicals, and for the production of biodegradable plastics and polymers. Other potential applications include biocompatible polylactic acids for biomedical applications. These polylactic acids have potential applications as prosthetic devices, controlled drug delivery in humans, and food packaging. Additionally, lactic acid may also be used for the synthesis of ethanol resulting in a cost efficient alternative fuel source.

Although some biodegradable polymers are used in medical applications, the vast majority of high-volume consumer plastics continue to be composed of petroleum-based materials, which are essentially nondegradable. Recent events, such as rising costs of petroleum and the environmental costs associated with waste disposal, have made biodegradable polymers economically attractive. The food-processing industry generates large volumes of carbohydrate containing wastes, which are ideal substrates for bioconversion to useful, high-value products, such as lactic acid and its derivatives.

Soybean production is the second largest cash crop in the U. S. behind corn. Most soybeans are used traditionally for soybean meal and oil production. A metric ton of soybeans yields 800 kg of protein-rich meal and 183 kg of oil. The soybean hull, also known as the seed coat, is a byproduct of soybean processing. For every metric ton of soybean processed, about 100 kg of soybean hull is produced which is then disposed of for two American cents per pound. On a dry mass basis, the hulls constitute about 8% to 10% of the total seed, depending on the variety and the seed size. The hull is a hard water-resistant material, which protects the cotyledons and hypocotyls from damage. The soybean hull contains lignocellulose, which is any of several closely related substances constituting the essential part of woody cell walls of plants and consisting of cellulose intimately associated with lignin. Analysis of the soybean hull indicates that it is composed of carbohydrates (80% to 85%), protein (8% to 10%), ash (5% to 8%), and lipids (1%) on a dry mass basis. The dry soybean hull has about 7% to 8% moisture.

The use of microorganisms to generate lactic acid from fermentation of sugars, such as starch, is well known. Various manifestations of the microorganisms have been demonstrated including the use of immobilized and substrate attached microorganisms. For example, lactic acid has been successfully produced from the fermentation of starch carried out by *Lactobacillus amylovorous* immobilized in porous beads. See Lactic Acid Fermentation From Enzyme-Thinned Starch With Immobilized *Lactobacillus amylovorus*, Ji Yan, R. Bajpai, E. Iannotti, M. Popovic, and R. Mueller, *Chem. Biochem. Eng. Q.* 15 (2) 59–63 (2001).

U.S. Pat. No. 6,280,985 ('985) issued on Aug. 28, 2001 discloses a process for the separation and purification of lactic acid from a fermentation medium wherein the lactic acid is essentially in the form of a salt or salts. In the process of '985, the lactic acid producing microorganisms are separated from the other components of the fermentation medium forming a salt solution. The resultant solution is acidified to a pH below or equal to 3, and passed over a cation exchange resin to give lactic acid having a fraction with maximum of 25% lactic acid salts (dry weight). This fraction is then subjected to bipolar fractionating electrodialysis, and other purification/concentration techniques.

U.S. Pat. No. 5,932,455 ('455) issued on Aug. 3, 1999 discloses a method for preparing pure lactic acid or salt thereof by fermentation. The preparation process comprises a bioreactor refreshing cycle and a lactic acid production cycle, wherein during the production cycle a solution comprising substantially pure feedstock is recycled though a bioreactor containing refreshed microorganism cells, the lactic acid produced being neutralized by adding an alkali, and the recycling is discontinued when the alkali consumption is substantially diminished. During the refreshing cycle the microorganism cells are refreshed by recycling though the bioreactor a carbohydrate solution enriched with nutrients, thus replenishing the capacity of the microorganisms to produce an acid. Lactate is recovered or converted into lactic acid or other salt.

The use of food-processing waste to produce lactic acid and to simultaneously carry out fermentation and hydrolysis in the production of lactic acid is known. U.S. Pat. No. 6,319,382 issued on Nov. 20, 2001 describes a fermentative production and isolation of lactic acid from a sugar-containing fermentation liquid in a fermentor by means of lactic acid forming bacteria, in which whey protein is present or added as a nutrient substrate for the lactic acid-forming bacteria, wherein at least one protease is added to the fermentor during the fermentation so that hydrolysis of protein to amino acids takes place simultaneously with the fermentation of sugar into organic acid, and wherein lactic acid resulting from the fermentation is isolated from the fermentation liquids. Ammonia is preferably added resulting in the formation of ammonium lactate, and lactic acid is preferably isolated by a process involving ultra filtration, ion exchange, conventional electrodialysis and electrodialysis with bipolar membranes.

U.S. Pat. No. 5,464,760 ('760) issued on Nov. 7, 1995 discloses a fermentation and recovery process for lactic acid production. The method of '760 is used to convert starch to glucose and fermenting the glucose to form lactic acid. The method includes simultaneous saccharification and fermentation through the use of a consortium of bacterial strains. The invention of '760 involves the bioconversion of industrial food waste, such as potato waste, corn, rice, cheese whey, cane sugars, beet sugars or the like, containing starch to lactic acid suitable for conversion to photodegradable or biodegradable plastics. The invention first liquefies the waste using an alpha-amylase enzyme.

Additionally, scientist have successfully used simultaneous saccharification and fermentation to produce lactic acid from cellulose using a combination of *Tchoderma reesei* as a cellulose for saccharification and *Lactobacillus delbrueckii* as the lactic acid producing microorganism. See Communications to the Editor: Simultaneous Saccharification and Fermentation of Cellulose to Lactic Acid, Shin-ichiro Abe and Motoyoshi Takagi, *Biotechnology and Bioengineering*, 37, 93–96 (January 1991).

None of the above inventions and patents, taken either singularly or in combination, is seen to describe the instant invention as claimed.

SUMMARY OF THE INVENTION

The present invention relates to a method for producing lactic acid from agricultural feedstock, preferably from lignocellulose containing feedstock such as soybean hulls, by size reducing, hydrolyzing, and fermenting the feedstock to produce lactic acid. The size reduction may be performed either mechanically or through steam explosion. The hydrolysis may be either enzyme or acid hydrolysis. Furthermore, the hydrolysis and fermentation steps may either be carried out separately or simultaneously. The simultaneous hydrolysis and fermentation involves the use of an enzyme hydrolysis and microbial fermentation in the same vessel at the same time. Steam explosion refers to the treatment of lignified biomass with high-pressure steam for short periods followed by rapid decompression.

The feedstock may be produced through protein extraction followed by separation techniques, involving filtration, centrifuge and membrane filtration, that separates the liquids from the solids producing the solid feedstock and producing liquids. The liquids may be subjected to protein precipitation to generate protein for alternative uses such as protein animal feed. Also, following fermentation and lactate recovery, the resultant material is filtered into solid and liquid fractions. The solid fraction can be used for alternative uses such as protein animal feed, while the liquid fraction which contains the lactic acid is further purified.

An aspect of the present invention is to provide a process by which lactic acid can be produced and isolated from renewable resources containing high amounts of lignocellulose, such as soybean hulls, and from agricultural waste materials. Using such renewable feed stock presents several environmental benefits. As an alternative to petroleum based polymers, production of lactic acid polymers uses substantially less fossil fuel and releases a lower amount of carbon dioxide than comparable petroleum-based plastics. Carbon dioxide in the atmosphere is removed when the feedstock is grown and is returned to the earth when the polymer is degraded. Additionally, products comprised of lactic acid-based polymers can be recycled back to the monomer and reused. At the end of its lifecycle, a product can be broken down into its simplest form with no signs of any remains.

Yet another aspect of the present invention is to provide a process by which lactic acid can be generated from agricultural waste materials, such as the soybean hull, which has proven to be difficult in the past. The present invention allows the soybean hull to be hydrolyzed into monomeric sugars and fermented into lactic acid, which is recovered and purified for use in industry.

An additional aspect of the present invention is to provide a process which may be automated to produce high yields of lactic acid. High yield lactic acid may result in a cost efficient fuel synthesis.

A further aspect of the present invention is to provide a process for forming stereospecific lactic acid for use in polymer generation. The selection of microorganism for fermentation allows stereospecific lactic acid to be formed as desired. The choice of microorganism also permits the use of thermophilic bacteria in the production of lactic acid therefore reducing the risk of contamination by other bacteria.

Yet an additional aspect of the present invention is to reduce the cost of generating biodegradable polymeric materials from agricultural waste products. Unlike other biomass feedstocks, which are widely dispersed, bulky, and have high moisture content, the soybean hull are concentrated at the processing sites, have low moisture content and have relatively small particle size distribution. Furthermore, it is more cost efficient to utilize lignocellulosic glucose (but not starch) because it is a cheaper raw material.

A further aspect of the present invention is to increase the profitability of the soybeans industry by diversifying the product base and adding value to low value by-products. The present invention facilitates the production of lactic acid from soybean hulls, while permitting the retrieval of protein concentrates for use in animal feed.

These and other objects of the present invention will become readily apparent upon further review of the following drawings and specification.

BRIEF DESCRIPTION OF THE DRAWING

The novel features of the described embodiments are specifically set forth in the appended claims; however, embodiments relating to the structure and process of making the present invention, may best be understood with reference to the following description and accompanying drawing.

The sole FIGURE shows a process flowchart depicting alternative procedures for production of lactic acid from soybean hulls according to the present invention.

Similar reference characters denote corresponding features consistently throughout the attached drawing.

DETAILED DESCRIPTION OF PREFERRED EMBODIMENTS

The method of the present invention can be understood with reference to the sole FIGURE, which shows a flowchart 12. The agricultural feedstock, such as soybean hulls, must first be converted to monomeric sugars by pretreatment and enzymatic saccharification. Initially, a pretreatment procedure is carried out by diluting caustic extraction of soluble protein fraction. A mixture containing from about 30% to about 70% dilute caustic soda (NaOH) solution having 1.5% in water and from about 30% to about 70% soybean hull is agitated at from about 25° C. to about 75° C. for about 1 to 5 hours, as denoted in the FIGURE by numeral 14. A soluble protein fraction is extracted from the soybean hull, and removed with the liquid when the solid soybean hull is separated from the mixture by filtration, denoted by the numeral 16. The protein in the liquid fraction can be precipitated, as denoted by the numeral 18, by lowering the liquid pH below the isoelectric point of the protein. The protein is useful in a variety of protein applications including but not limited to, animal feed supplement, denoted by the numeral 20, pharmacophore investigation, and fertilizer.

Filtration is achieved by processes including, but not limited to, membrane filtration with or without forced air pressure gradient and/or hydraulic pressure gradient, centrifugal separation, and vortex separation. The resultant solution forms a structural carbohydrate substrate.

In addition to the soybean hull, the present invention may utilize feedstock generated from corn fiber, rice, beets, cane, and the like. The present invention may also be used for newspaper and wood, although newspaper has the negative environmental impact of heavy metal content of inks. Reclaimed wood may also contain toxic chemicals. Natural untreated agricultural resources have fewer pollutants and can be used in food, technical applications and plastics without concern about pollutants such as heavy metals. Furthermore, protein antioxidant extracted from the hull may be suitable for a variety of potential uses, such as the investigation of potential pharmacophores for medicinal research.

As used herein, all percentages (%) are percent weight-to-weight, also expressed as weight/weight %, % (w/w), w/w, w/w % or simply %, unless otherwise indicated.

The pretreatment also includes a mechanical disruption technique, denoted 22 in the sole FIGURE. Mechanical disruption techniques include, but are not limited to, steam explosion and wet/dry grinding. The steam explosion method involves placing the structural carbohydrate substrate containing from about 3% to about 25% water in a pressure chamber. The chamber is pressurized with dry steam to about 1.25 to about 5 atmospheres, and maintained until the substrate reaches temperatures in excess of the boiling point of water at atmospheric pressure, when it is explosively decompressed to atmospheric pressure or below, causing rapid boiling of the water component of the substrate and consequent disruption of the substrate structure. The temperature and pressure combination of steam explosion is used to break down material.

The wet/dry grinding methodology involves grinding by abrasive surface, or knife milling may be employed to increase the substrate surface area.

Following pretreatment, bioprocessing is performed in two steps, which may occur sequentially. The two steps are hydrolytic chain scission of cellulose/hemicellulose, and microbial conversion, fermentation, of resulting sugars to lactic acid. The hydrolytic chain scission can be carried out by either enzyme hydrolysis 24 or acid hydrolysis 26, as is well known in the art. The hydrolysis of steam exploded soybean hulls may involve the use of commercial xylanase and cellulase enriched with beta-glucosidase.

In carrying out the enzyme hydrolysis 24, various cellulose enzymes, such as that available from Genecor (e.g., spezyme CP) or from Iogen (e.g., DP 138) may be employed in the hydrolysis phase. The process is conducted in aqueous solution according to the enzyme manufacturer instructions, which may include the use of a pH buffer, elevated temperature, and agitation. Many other proteases are commercially available and may be substituted herein.

Acid hydrolysis 26 may be effected by placing the pretreated substrate in an acidic solution at elevated temperature with agitation. The acid must be neutralized achieving a pH suitable for microbial activity prior to fermentation.

The next step involves the fermentation, as denoted by numeral 28, of simple sugars to lactic acid and is achieved with the aid of lactic acid producing bacteria, such as the bacteria *Lactobacillus pentosus* at 37° C. with light agitation. As the bacteria metabolizes the sugar and produces lactic acid, the pH of the solution is decreased. This decrease in pH must be controlled to prevent conditions toxic to the microorganism.

Other alternative lactic acid-forming bacteria, or combinations of more than one lactic acid bacteria, may be used. Suitable lactic acid producer organisms include natural and/or selected microorganisms or microorganisms produced by adaptation or mutated to produce a desired lactic acid. Producer organisms include lactic acid bacteria, such as those of the genera *Aerococcus, Bacillus, Carbobacterium, Enterococcus, Erysipelothrix, Gemella, Globicatella, Lactobacillus, Lactococcus, Leuconostoc, Pediococcus, Streptococcus, Tetragenococcus* and *Vagococcus*. For example, other bacteria of the genus *Lactobacillus* which may be substituted include, but are not limited to, *L. heiveticus, L. delbrueckii, L. casei, L, acidophilus, L. amylovorus, L. leichmanii* or *L. bulgaricus. L. amylovorus* (produces cell-bound glucoamylase and degrades starch), and *L. pentosus* are available from ATCC, a nonprofit bioresource center of Manassas, Va. *L. delbrueckii* is available from the Institute for Fermentation in Osaka, Japan.

The lactic acid forming bacteria may be used alone or together with another microorganism, for example as a co-culture. It is also possible to substitute or add moulds, such as Rhizopus, as a lactic acid forming microorganism.

The use of different strains of a lactic acid bacteria makes it possible to form L(+), L(−) or D(−) as well as mixtures of L(+)/(−) and D(−). The term "lactic acid" is used herein to refer to any one of these types of lactic acid or a mixture thereof.

Alternatively, the bioprocessing may be performed in one step with simultaneous saccharification and fermentation, as denoted by the numeral 30 in the sole FIGURE. The structural carbohydrate substrate is placed in a single container, and the enzymes, microorganisms, nutrients and buffers are all added to the single container to perform both the hydrolysis and fermentation in a single step. This method is followed by lactate recovery, as denoted by the numeral 32. *Trichoderma reesei* is a fungi which may be added to the simultaneous saccharification and fermentation as a source of high temperature cellulose for simultaneous saccharification and fermentation. *Trichoderma reesei* is also available from ATCC. *Lactobacillus delbrueckii*, which has a high temperature resistance, is a preferred lactic acid producing microorganism for use in the simultaneous saccharification and fermentation embodiment. Additionally, *Bacillus stearothermophilus* is also a suitable microorganism for the simultaneous saccharification and fermentation because it also produces lactic acid at relatively high temperatures (60° C. to 70° C.). Furthermore, *B. stearothermophilus* can be grown either aerobically or anaerobically. In the anaerobic mode, L-lactic acid is the main product.

PH controls, which may be used, include but are not limited to a pH buffer consisting of sodium citrate and citric acid or $CaCO_3$. $CaCO_3$ may be added to the solution in an amount from about 5% to about 40% of dry solids substrate material. Free calcium ions in the solution combine with molecules of lactic acid to form the relatively pH neutral dilactide, calcium lactate. When fermentation is complete, the lactic acid can be recovered from the dilactide by addition of acid, as is well known in the art. It is also possible to maintain the desired pH by means of various bases such as ammonia, NaOH, and $Ca(OH)_2$.

The fermentation, or lactate recovery for the single step process, is followed by filtration, as denoted by the numeral 34, wherein the solids are removed to be used in the same manner as the protein precipitate 18. The liquid fermentation product is purified, as denoted by the numeral 36, and lactic acid 38 is produced.

Since *Lactobacillus pentosus* has simultaneous aerobic and anaerobic activity, the oxygen pressure should be carefully controlled to maximize yield. Alternatively, a high temperature microorganism may be used in conjunction with the cellulose enzyme for simultaneous saccharification and fermentation.

The invention may be understood by reference to the following example, which is included to demonstrate an embodiment of the present invention.

In the practice of the present invention, the protein extraction occurs first as demonstrated by the following examples. Soybean hull was purchased from Purdue and ADM both with and without knife mill processing. The first sample was in the form of dry chips having average diameters ranging in size from 1 to 4 mm. The second sample retained much of the shape of the soybean from which it was stripped. A sodium hydroxide solution was prepared by dissolving 1.4% of sodium hydroxide pellets in deionized water.

A hundred grams (100 g) of knife milled soy hull from Purdue was placed in a 2L Erlenmeyer flask with 1.25 L of the sodium hydroxide solution. The pH of the mixture was approximately 12. The mixture was stirred by hand with a glass stirring rod until all the feed was wetted. The flask was placed in a New Brunswick Scientific C-76 Classic orbital shaker bath at 60° C. and agitated for three hours at 125 RPM.

The contents of the flask were emptied into a Buchner funnel outfitted with a piece of coarse grade 60 Wattman filter paper. The liquid and solid fractions were separated by vacuum filtration. The liquid fraction, containing the dissolved protein, was placed in an appropriate container and saved for later processing. The solids were rinsed three times with deionized water, and the rinse water was discarded. The filtrate was retained for later experimentation, and the solids were placed in a warm, dry area until the sample contained 15% water or less, which usually required three to four days. The dried sample was transferred to a sealed container for storage. The procedure was repeated until a total of 1000 g protein extracted dried biomass was accumulated.

Steam explosion was the next step carried out. The solids content of the biomass was determined prior to steam explosion, as is well known in the art. After placing 1 kg of protein extracted biomass in the reactor, it was sealed, steam pressurized to 15 psi, and held for 90 seconds prior to explosive depressurization. This corresponds to an severity factor ($R_0$) of 3.8 as defined by the following equation:

$$R_1 = \int_0^t \exp \frac{(T - T_b)}{P} dt,$$
$$R_0 = \log R_1$$

where $R_0$ is the steam explosion severity factor, T is the steam explosion temperature, $T_b$ is the boiling temperature of water and P is the steam explosion pressure. The biomass was then rinsed. In the rinsing process the biomass was diluted to less than 2% solids. The diluted biomass was then centrifuged and decanted to increase the solids content to 6.5±0.5%.

Enzyme hydrolysis was carried out next. A buffering solution was prepared from citric acid and sodium citrate. Twenty grams (20 g) of enzyme grade citric acid, like that available from FisherBiotech #BP339-500, was dissolved in one liter (1L) distilled deionized water. Enzyme grade sodium citrate, like that available from FisherBiotech #BP327-1, was slowly added with constant agitation to adjust the solution pH to 4.7. Measurement of pH was performed with a Thermo Orion model 420 A+ pH meter with a Thermo Orion model 9157BN electrode.

The buffering solution was added to 100 g (wet weight) of steam exploded material in a 250 mL Erlenmeyer flask as necessary to adjust the pH to 5.0±0.2. The flask was sterilized at 121° C. for 15 minutes. Approximately one milliliter (1 mL) of cellulose enzyme (Spezyme CP from Genencor International Inc. of Finland) was added to the mixture, and the mixture was placed on the orbital shaker bath at 125 RPM and 50° C. for 72 hours.

The fermentation step followed the enzyme hydrolysis. A freeze-dried sample of the bacteria *Lactobacillus pentosus* (ATCC #8041) was obtained and rejuvenated according to the manufacturers instructions in sterile Difco Lactobacilli MRS Broth (product #288130), and cultures were maintained on sterile Difco Lactobacilli Agar AOAC (product #290010).

The microorganism was separated from approximately 50 mL of cultured MRS broth by centrifugation. The separated cells were washed three times with distilled, deionized, sterile water. These cells were added to the 250 mL Erlenmeyer flask containing the hydrolyzed biomass under sterile conditions. After inoculation, the flask was placed on the orbital shaker bath at 124 RPM and 30° C. for a 72-hour fermentation period.

The results were analyzed. The lactic acid containing liquid fraction was separated from the fermentation flask by centrifugation. The liquid was analyzed on a Shimadzu High Performance Liquid Chromatograph outfitted with a lead column from Benson Polymeric Inc. Distilled, deionized water was used as the carrier, 20 μL was the sample injection volume at a flow rate of 0.5 μL per minute, and the temperature was 85° C. Comparison with lactic acid standards obtained from Labchem (product #LC16020-1) indicated a lactic acid concentration of approximately 1 g/mL. This corresponds to a conversion rate of 20% from dry solid mass in steam-exploded biomass to lactic acid.

It is to be understood that the present invention is not limited to the embodiments described above, but encompasses any and all embodiments within the scope of the following claims.

What is claimed is:

1. A method for production of lactic acid, comprising the steps of:

steam exploding a structural carbohydrate substrate, derived from a protein-rich lignocellulose-containing feedstock, by placing the structural carbohydrate substrate containing from about 3% to about 25% water in a pressure chamber, pressurizing the steam chamber with dry steam greater than about 1.24 atmospheres, maintaining the pressure until the structural carbohydrate substrate reaches temperatures in excess of the boiling point of water at atmospheric pressure, and explosively decompressing the pressure to a pressure no greater than atmospheric pressure thereby generating a disrupted carbohydrate substrate;

hydrolyzing the disrupted carbohydrate substrate; and fermenting the resulting hydrolyzed carbohydrate substrate to produce a fermented substrate containing lactic acid.

2. The method of claim 1, further comprising the steps of:
extracting protein from a protein-rich lignocellulose-containing renewable feedstock by agitating a dilute caustic soda solution containing from about 30% to about 70% NaOH, and about 30% to about 70% protein-rich lignocellulose-containing renewable feedstock at about 25° C. to about 75° C. for about 1 to 5 hours; and
separating the protein-rich lignocellulose-containing renewable feedstock into a liquid fraction and a solid fraction by extracting the solid fraction forming a structural carbohydrate substrate and removing the liquid fraction therefrom using filtration.

3. The method of claim 2, further comprising the steps of:
precipitating protein from the liquid fraction by lowering the liquid pH below the isoelectric point of the protein.

4. The method of claim 1, wherein:
the step of hydrolyzing the disrupted carbohydrate substrate and fermenting the resulting hydrolyzed carbohydrate substrate to form a fermented substrate is carried out simultaneously; and
the step of hydrolyzing the disrupted carbohydrate substrate is carried out by enzyme hydrolysis.

5. The method of claim 1, wherein:
the step of hydrolyzing the disrupted carbohydrate substrate is carried our by acid hydrolysis.

6. The method of claim 1, wherein:
the step of hydrolyzing the disrupted carbohydrate substrate is carried out by enzyme hydrolysis.

7. The method of claim 4, further comprising the step of:
recovering lactate from the resultant fermented substrate.

8. The method of claim 1 further comprising the step of:
filtering the fermented substrate; and
recovering solid and liquid fermentation products therefrom.

9. The method of claim 8, further comprising:
purifying the liquid fermentation products to separate and recover the lactic acid therefrom.

10. The method of claim 2, further comprising:
precipitating protein from the liquid fraction.

11. A method for production of lactic acid from a protein-rich lignocellulose-containing natural renewable feedstock, comprising the steps of:
reducing the size of particles of a structural carbohydrate substrate derived from the protein-rich lignocellulose-containing feedstock through a mechanical disruption technique;
hydrolyzing the resultant disrupted carbohydrate substrate; and
fermenting the resulting hydrolyzed carbohydrate substrate to produce lactic acid.

12. The method of claim 11, wherein:
the size of the particles is reduced by steam exploding the structural carbohydrate substrate by placing the structural carbohydrate substrate containing from about 3% to about 25% water in a pressure chamber, pressurizing the steam chamber with dry steam greater than about 1.24 atmospheres, maintaining the pressure until the structural carbohydrate substrate reaches temperatures in excess of the boiling point of water at atmospheric pressure, and explosively decompressing the pressure to a pressure no greater than atmospheric pressure thereby generating a disrupted carbohydrate substrate.

13. The method of claim 11, further comprising the steps of:
extracting protein from the natural protein-rich lignocellulose-containing renewable feedstock by agitating a dilute caustic soda solution containing from about 30% to about 70% NaOH, and about 30% to about 70% protein-rich lignocellulose-containing renewable feedstock at about 25° C. to about 75° C. for about 1 to 5 hours; and
separating the natural protein-rich lignocellulose-containing renewable feedstock into a liquid fraction and a solid fraction by extracting the solid fraction forming a structural carbohydrate substrate and removing the liquid fraction therefrom using filtration.

14. The method of claim 11, further comprising the steps of:
precipitating protein from the liquid fraction by lowering the pH below the isoelectric point of the protein.

15. The method of claim 11, wherein:
the step of hydrolyzing the disrupted carbohydrate substrate and fermenting the resulting hydrolyzed carbohydrate substrate to form a fermented substrate is carried out simultaneously; and
the step of hydrolyzing the disrupted carbohydrate substrate is carried out by enzyme hydrolysis.

16. The method of claim 11, wherein:
the step of hydrolyzing the disrupted carbohydrate substrate is carried our by acid hydrolysis or enzyme hydrolysis.

17. The method of 15, further comprising the step of:
recovering the lactate from the resultant fermented substrate.

18. The method of claim 11 further comprising the step of:
filtrating the fermented substrate; and
recovering solid and liquid fermentation products therefrom.

19. The method of claim 18, further comprising:
purifying the liquid fermentation products to separate and recover the lactic acid therefrom.

20. The method of claim 13, further comprising:
precipitating protein from the liquid fraction.

\* \* \* \* \*